(12) United States Patent
Qian et al.

(10) Patent No.: US 11,918,976 B2
(45) Date of Patent: Mar. 5, 2024

(54) ELECTROSTATIC ADSORPTION MASK

(71) Applicant: Beijing FUNATE Innovation Technology Co., LTD., Beijing (CN)

(72) Inventors: Li Qian, Beijing (CN); Yu-Quan Wang, Beijing (CN); Li Fan, Beijing (CN)

(73) Assignee: Beijing FUNATE Innovation Technology Co., LTD., Beijing (CN)

( * ) Notice: Subject to any disclaimer, the term of this patent is extended or adjusted under 35 U.S.C. 154(b) by 708 days.

(21) Appl. No.: 17/097,277

(22) Filed: Nov. 13, 2020

(65) Prior Publication Data

US 2022/0023828 A1 Jan. 27, 2022

(30) Foreign Application Priority Data

Jul. 23, 2020 (CN) .......................... 202010718377.6

(51) Int. Cl.
*B01J 20/20* (2006.01)
*A41D 13/11* (2006.01)
(Continued)

(52) U.S. Cl.
CPC ......... *B01J 20/205* (2013.01); *A41D 13/1161* (2013.01); *A41D 31/145* (2019.02); *A61L 9/014* (2013.01); *A62B 18/025* (2013.01); *A62B 18/084* (2013.01); *A62B 23/025* (2013.01); *B01D 39/2055* (2013.01); *B01D 46/0032* (2013.01); *B01D 46/4245* (2013.01); *B01D 46/546* (2013.01); *B01J 20/28035* (2013.01); *B01J 20/28085* (2013.01); *A61L 2209/14* (2013.01); *A61L 2209/22* (2013.01);
(Continued)

(58) Field of Classification Search
CPC ... A62B 18/084; A62B 18/025; A62B 23/025; C01B 2202/02; C01B 2202/08; C01B 2202/06; A41D 13/1161; A41D 13/1192; A41D 13/11; B32B 29/002; B32B 5/26; B01D 46/546; B01D 39/2065; B01D 39/2055; B01D 39/2041; B01D 2239/065; B01D 2239/025; B01J 20/205
See application file for complete search history.

(56) References Cited

U.S. PATENT DOCUMENTS

| 10,322,303 | B2 | 6/2019 | Qian et al. |
| 2016/0015098 | A1* | 1/2016 | Conlon ............... A41D 13/1115 29/428 |
| 2016/0016022 | A1 | 1/2016 | Qian et al. |

FOREIGN PATENT DOCUMENTS

| CN | 105231525 | 1/2016 |
| CN | 105433468 | 3/2017 |

(Continued)

*Primary Examiner* — Ophelia A Hawthorne
(74) *Attorney, Agent, or Firm* — ScienBiziP, P.C.

(57) ABSTRACT

An electrostatic adsorption mask is provided. The mask comprises two straps, a mask body, a filtering layer and a tiny power. The filtering layer is located in the mask body and comprises a first carbon nanotube layer, a second carbon nanotube layer and an insulated porous layer. The insulated porous layer is located between the first carbon nanotube layer and the second carbon nanotube layer. The first carbon nanotube layer and the second carbon nanotube layer are electrically coupled with the tiny power. An electric field is existed between the first carbon nanotube layer and the second carbon nanotube layer.

12 Claims, 10 Drawing Sheets

(51) Int. Cl.

| | | |
|---|---|---|
| | *A41D 31/14* | (2019.01) |
| | *A61L 9/014* | (2006.01) |
| | *A62B 18/02* | (2006.01) |
| | *A62B 18/08* | (2006.01) |
| | *A62B 23/02* | (2006.01) |
| | *B01D 39/20* | (2006.01) |
| | *B01D 46/00* | (2022.01) |
| | *B01D 46/42* | (2006.01) |
| | *B01D 46/54* | (2006.01) |
| | *B01J 20/28* | (2006.01) |

(52) U.S. Cl.
 CPC ........... *B01D 2239/0241* (2013.01); *B01D 2239/025* (2013.01); *B01D 2239/0435* (2013.01); *B01D 2239/1216* (2013.01); *B01D 2275/10* (2013.01)

(56) References Cited

FOREIGN PATENT DOCUMENTS

| | | |
|---|---|---|
| JP | H07-24077 | 1/1995 |
| TW | M510761 | 10/2015 |

\* cited by examiner

ELECTROSTATIC ADSORPTION MASK

CROSS-REFERENCE TO RELATED APPLICATIONS

This application claims all benefits accruing under 35 U.S.C. § 119 from China Patent Application No. 202010718377.6, filed on Jul. 23, 2020, in the China Intellectual Property Office, the contents of which are hereby incorporated by reference.

FIELD

The subject matter herein generally relates to a Electrostatic adsorption mask.

BACKGROUND

At present, most of masks sold on the market only have a limited filtering function and cannot filter the tiny dust of PM2.5 in the air. For masks with higher filtration efficiency, the main purpose is to prevent pollutants from entering the human body by blocking. However, due to the need for normal breathing of people, the respiratory resistance of the mask cannot be too large, which creates a contradiction between the efficiency of dust suppression and the respiratory resistance.

BRIEF DESCRIPTION OF THE DRAWINGS

Implementations of the present technology will now be described, by way of embodiments, with reference to the attached figures, wherein.

DETAILED DESCRIPTION

The disclosure is illustrated by way of example and not by way of limitation in the figures of the accompanying drawings in which like references indicate similar elements. It should be noted that references to "another," "an," or "one" embodiment in this disclosure are not necessarily to the same embodiment, and such references mean "at least one."

It will be appreciated that for simplicity and clarity of illustration, where appropriate, reference numerals have been repeated among the different figures to indicate corresponding or analogous elements. In addition, numerous specific details are set forth in order to provide a thorough understanding of the embodiments described herein. However, it will be understood by those of ordinary skill in the art that the embodiments described herein can be practiced without these specific details. In other instances, methods, procedures and components have not been described in detail so as not to obscure the related relevant feature being described. Also, the description is not to be considered as limiting the scope of the embodiments described herein. The drawings are not necessarily to scale and the proportions of certain parts have been exaggerated to better illustrate details and features of the present disclosure.

Several definitions that apply throughout this disclosure will now be presented.

The term "contact" is defined as direct and physical contact. The term "substantially" is defined to be that while essentially conforming to the particular dimension, shape, or other feature that is described, the component is not or need not be exactly conforming to the description. The term "comprising," when utilized, means "including, but not necessarily limited to"; it specifically indicates open-ended inclusion or membership in the so-described combination, group, series, and the like.

Figure 1:
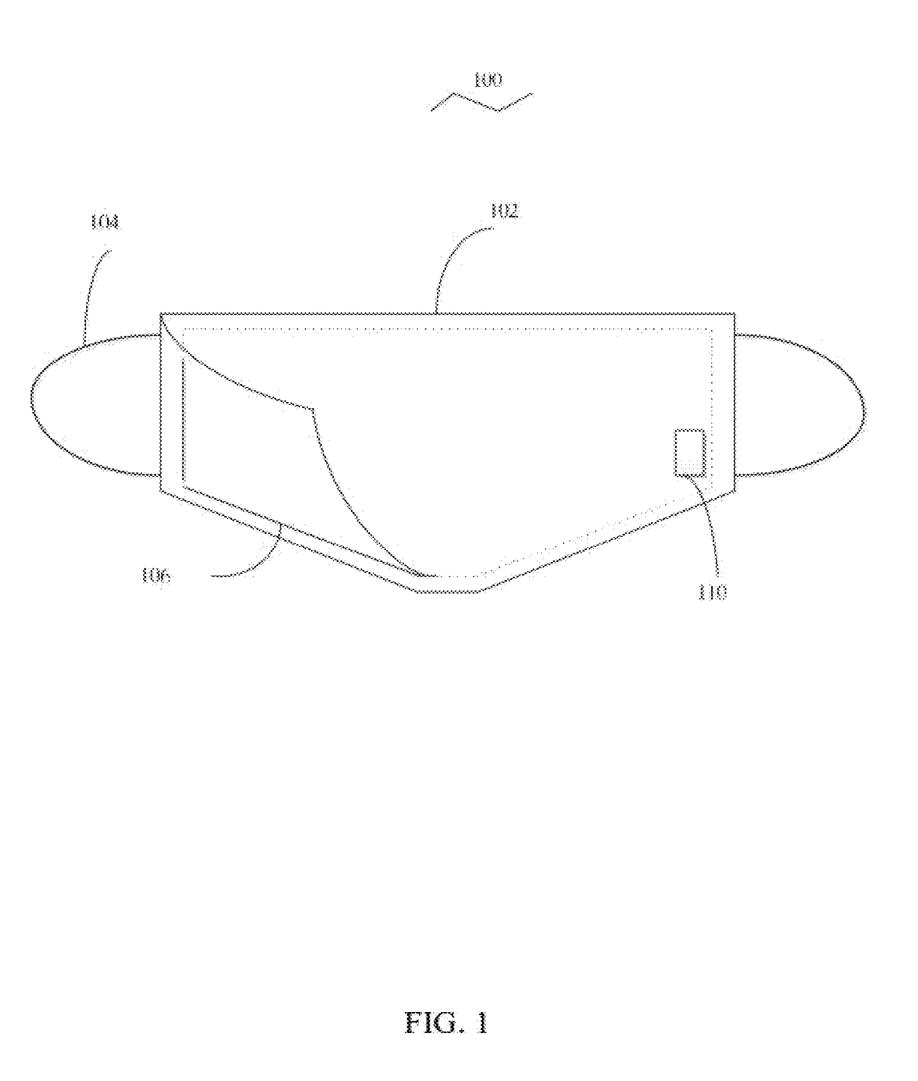
FIG. 1 is a sectional schematic view of an electrostatic adsorption mask according to a first embodiment.
Figure 2:
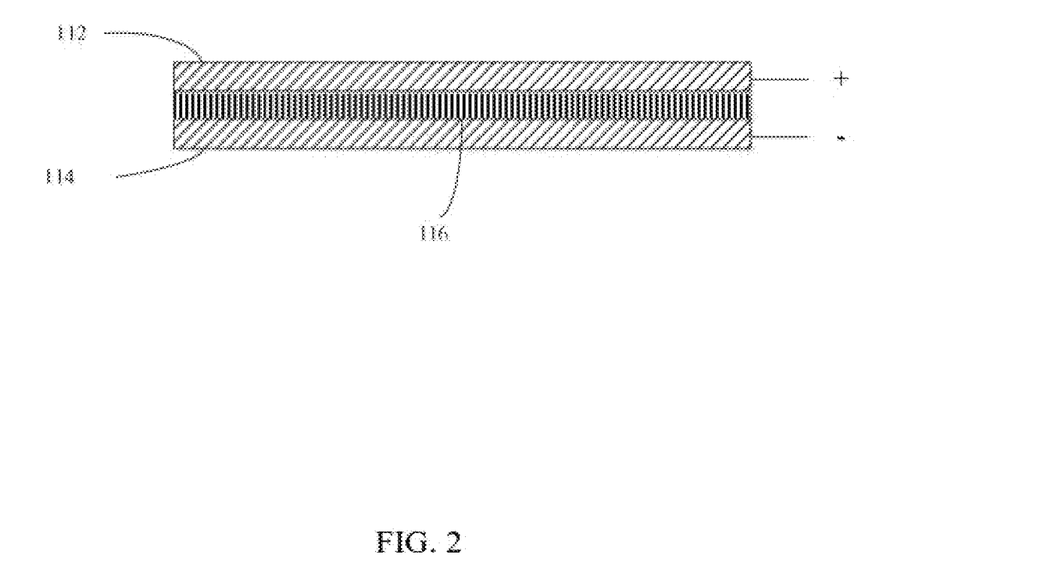
FIG. 2 is a schematic view of an internal structure of the electrostatic adsorption mask in FIG. 1.

Referring to FIGS. 1 and 2, an electrostatic adsorption mask 10 according to a first embodiment is provided. The Electrostatic adsorption mask 10 includes a mask body 102, two straps 104, a filtering layer 106, and a tiny power 110. The filtering layer 106 is located in the mask body 102, and comprises a first carbon nanotube layer 112, a second carbon nanotube layer 114 and an insulated porous layer 116. The insulated porous layer 116 is located between the first carbon nanotube layer 112 and the second carbon nanotube layer 114. The first carbon nanotube layer 112 and the second carbon nanotube layer 114 and electrically coupled with the tiny power 110. An electric field is formed between the first carbon nanotube layer 112 and the second carbon nanotube layer 114.

The mask body 102 comprises at least two layers, an inner layer and an outer layer. The filtering layer 106 is located between the inner layer and the outer layer. The two straps 104 are respectively arranged on opposite ends of the mask body 102. The two straps 104 are respectively arranged on two sides of the mask body 102 for hanging the mask on a user's ears. It can be understood that the two straps 104 can also be arranged in other ways, such as a sleeve type.

A material of the mask body 102 is preferably a light, thin and air-permeable material, which can be cotton, silk, gauze, non-woven fabric, hemp, fiber, nylon, spandex, polyester or polyacrylonitrile, etc. Preferably, the material of the mask body 102 is an air negative ion modified material. The air anions in the air anion modified material can reduce the activity of microorganisms and germs in the air, thereby inhibiting the survival of microorganisms or germs in the mask. At the same time, it can neutralize the positive ion-carrying dust, aerosol and other polluting particles in the air to achieve the purpose of purifying the air.

The mask body 102 is a two-layer structure. The mask body 102 is not limited to the two-layer structure in this embodiment and may also be a multi-layer structure. The mask body 102 can be an integrally formed structure or can be formed by combining at least two layers of structures by sewing or bonding. It can be understood that sizes of the at least two layers structure can be the same or different, as long as it is ensured that the at least two layers structure can comprise an accommodation space for placing the filtering layer 106. The shape of the mask body 102 can be arc, semi-circular, cup, rectangle or other desired shapes.

Preferably, the straps 104 are elastic. The arrangement of the strap 104 is not limited to this embodiment, as long as it can fix the mask with the sterilization function 100 on the user's face. For example, only one strap 104 can be provided. Two ends of the strap 104 are respectively located on the two sides of the mask body 102. The strap 104 can fix the mask with the sterilization function 100 on the back of the user's head. It can be understood that, the mask with the sterilization function 100 can have no straps in some embodiment. For example, a re-adhesive sticking piece is directly arranged on the inner surface of the mask body 102, and the sticking piece can be directly stuck to the skin so it will not cause pressure to the user and will not hinder the blood capillaries. The comfort of the user is greatly improved.

The filtering layer 106 is configured to filter micro particles and kill bacteria and viruses located inside and outside of the mask body 102. A thickness and a shape of the filtering layer 106 can be designed according to actual needs. The filtering layer 106 is a flexible layer including a plurality of micropores. Diameters of the micropores can be greater than 1 micrometer. The diameters of the micropores can be greater than 1 micrometer and less than 5 micrometers. Preferably, the diameters of the micropores can be in a range from 1 micrometer and to 2.5 micrometers. In some embodiments, diameters of the micropores are greater than 3 micrometers.

The insulated porous layer 116 separates the first carbon nanotube layer 112 and the second carbon nanotube layer 114. A thickness of the insulated porous layer 116 is in a range from 5 micrometers to 1 millimeter. A material of the insulated porous layer 116 can be cotton, silk, gauze, non-woven fabric, hemp, fiber, nylon, spandex, polyester or polyacrylonitrile, etc.

Figure 3:
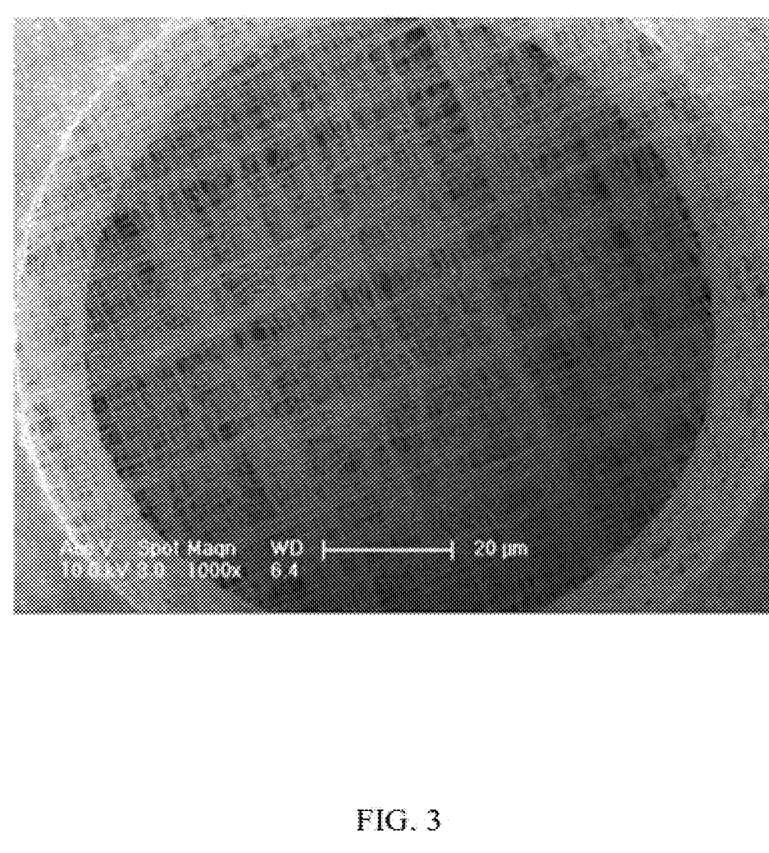
FIG. 3 shows a Scanning Electron Microscope (SEM) image of a carbon nanotube layer.
Figure 4:
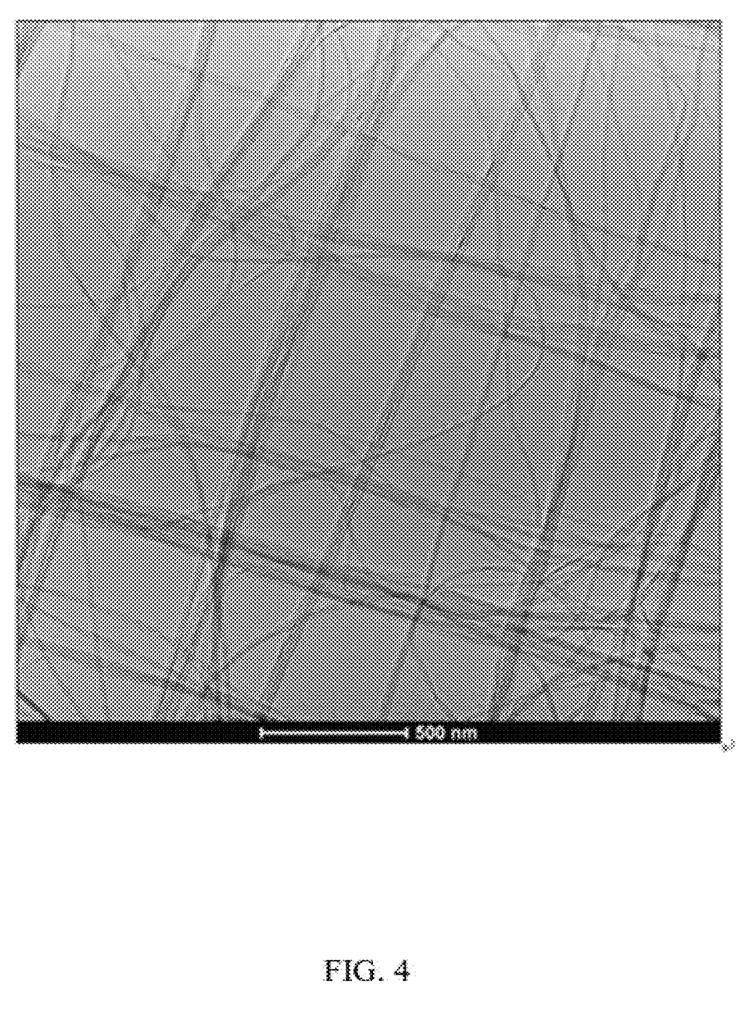
FIG. 4 shows a Transmission Electron Microscope (TEM) image of the carbon nanotube layer.

The first carbon nanotube layer 112 or the second carbon nanotube layer 114 is a carbon nanotube layer. In the following description, the carbon nanotube layer refers to the first carbon nanotube layer 112 or the second carbon nanotube layer 114. Referring to FIGS. 3 and 4, the carbon nanotube layer includes a plurality of carbon nanotubes joined by van der Waals attractive force therebetween. The carbon nanotube layer can be a substantially pure structure of carbon nanotubes, with few impurities. The carbon nanotube layer can be a freestanding structure so that the carbon nanotube layer can be supported by itself without a substrate. For example, if at least one point of the carbon nanotube layer is held, the entire carbon nanotube layer can be lifted while retaining its structural integrity.

The carbon nanotubes in the carbon nanotube layer can be orderly or disorderly arranged. The term 'disordered carbon nanotube layer' refers to a structure where the carbon nanotubes are arranged along different directions, and the aligning directions of the carbon nanotubes are random. The number of carbon nanotubes arranged along each different direction can be almost the same (e.g. uniformly disordered). The disordered carbon nanotube layer can be isotropic, namely, the carbon nanotube layer has properties identical in all directions of the carbon nanotube layer. The carbon nanotubes in the disordered carbon nanotube layer can be entangled with each other.

The carbon nanotube layer including ordered carbon nanotubes is an ordered carbon nanotube layer. The term 'ordered carbon nanotube layer' refers to a structure where the carbon nanotubes are arranged in a consistently systematic manner, e.g., the carbon nanotubes are arranged approximately along a same direction and/or have two or more sections within each of which the carbon nanotubes are arranged approximately along a same direction (different sections can have different directions). The carbon nanotubes in the carbon nanotube layer can be selected from single-walled, double-walled, and/or multi-walled carbon nanotubes. The carbon nanotube layer may include at least one carbon nanotube film. In other embodiments, the carbon nanotube layer is composed of one carbon nanotube film or at least two carbon nanotube films. In other embodiments, the carbon nanotube layer consists of one carbon nanotube film or at least two carbon nanotube films.

Figure 5:
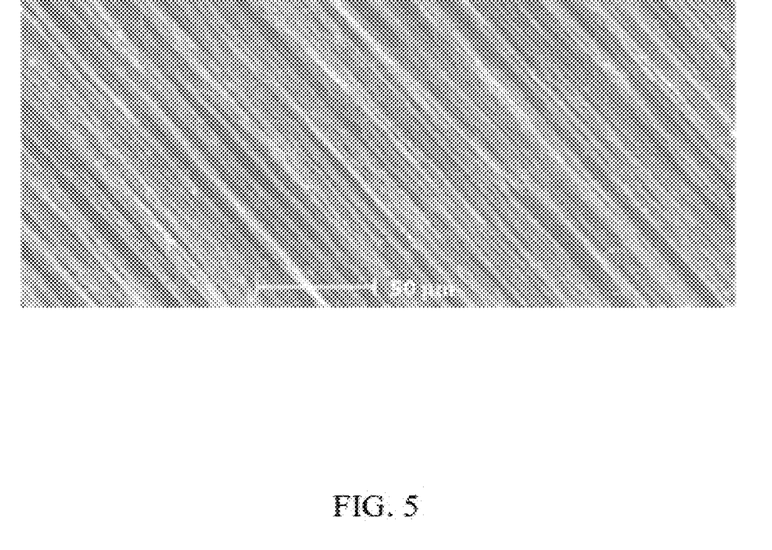
FIG. 5 shows an SEM image of a drawn carbon nanotube film.
Figure 6:
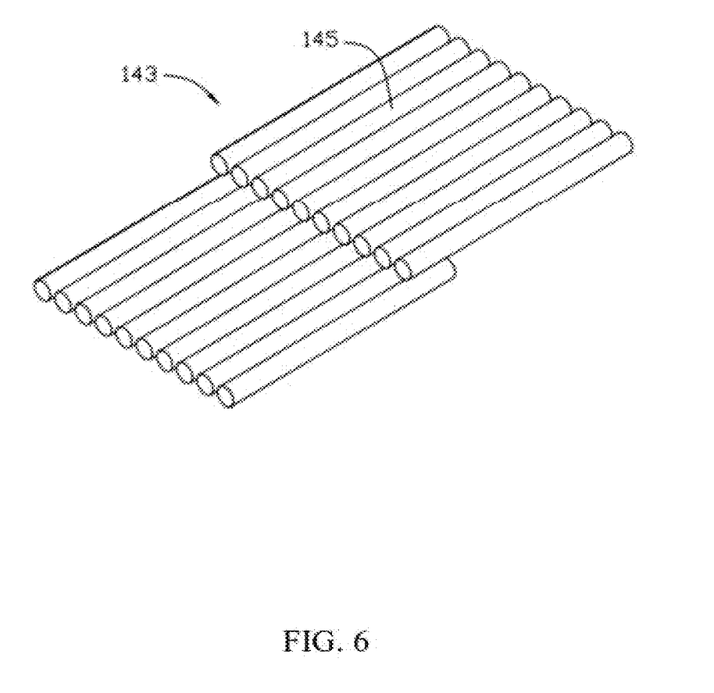
FIG. 6 is a schematic view of carbon nanotube segments in the drawn carbon nanotube film.

In one embodiment, the carbon nanotube film can be a drawn carbon nanotube film. Referring to FIG. 5, the drawn carbon nanotube film includes a number of successive and oriented carbon nanotubes joined end-to-end by van der Waals attractive force therebetween. The drawn carbon nanotube film is a freestanding film. Each drawn carbon nanotube film includes a number of successively oriented carbon nanotube segments joined end-to-end by van der Waals attractive force therebetween. Referring to FIG. 6, each carbon nanotube segment 143 includes a number of carbon nanotubes 145 substantially parallel to each other and joined by van der Waals attractive force therebetween. Some variations can occur in the drawn carbon nanotube film. The carbon nanotubes in the drawn carbon nanotube film are oriented along a preferred orientation. The drawn carbon nanotube film can be treated with an organic solvent to increase the mechanical strength and toughness of the drawn carbon nanotube film and reduce the coefficient of friction of the drawn carbon nanotube film. A thickness of the drawn carbon nanotube film may range from about 0.5 nanometers to about 100 micrometers. The drawn carbon nanotube film can be used as a carbon nanotube layer directly.

The carbon nanotubes in the drawn carbon nanotube film can be single-walled, double-walled, and/or multi-walled carbon nanotubes. The diameters of the single-walled carbon nanotubes may range from about 0.5 nanometers to about 50 nanometers. The diameters of the double-walled carbon nanotubes may range from about 1 nanometer to about 50 nanometers. The diameters of the multi-walled carbon nanotubes may range from about 1.5 nanometers to about 50 nanometers. The lengths of the carbon nanotubes may range from about 200 micrometers to about 900 micrometers.

The carbon nanotube layer may include at least two stacked drawn carbon nanotube films. The carbon nanotubes in the drawn carbon nanotube film are aligned along one preferred orientation. An angle can exist between the orientations of carbon nanotubes in adjacent drawn carbon nanotube films, whether stacked or adjacent. An angle between the aligned directions of the carbon nanotubes in two adjacent drawn carbon nanotube films may range from approximately 0 degrees to approximately 90 degrees (e.g. about 15 degrees, 45 degrees, or 60 degrees).

Figure 7:
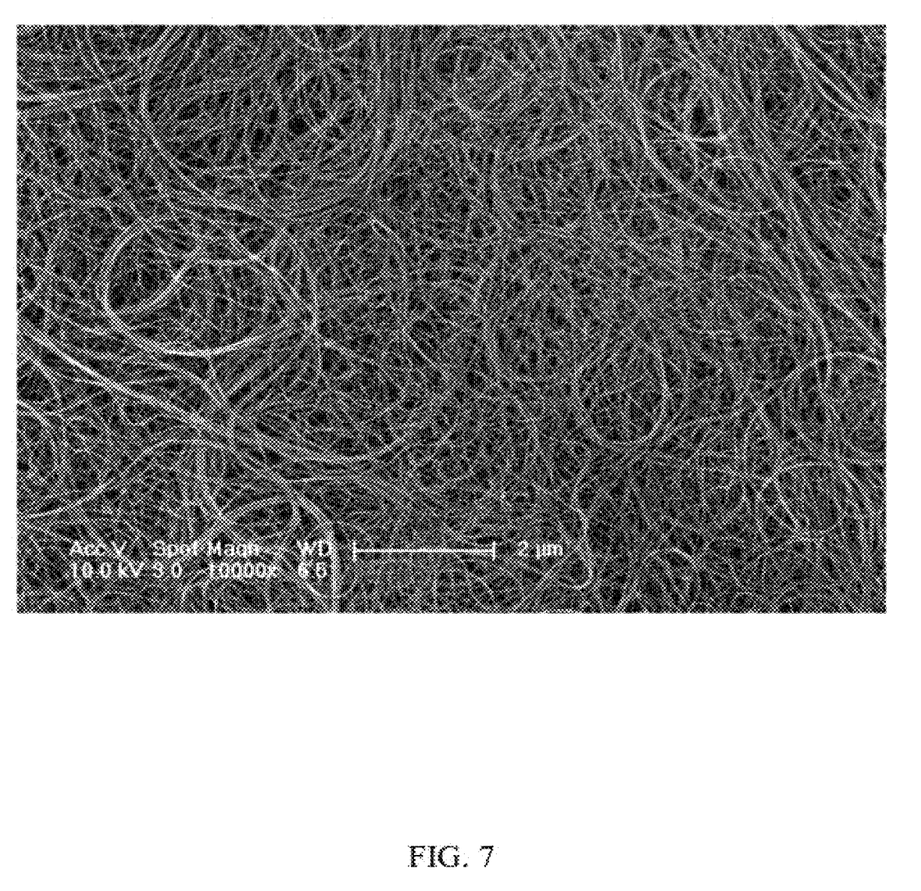
FIG. 7 shows an SEM image of a flocculated carbon nanotube film.

In other embodiments, the carbon nanotube film can be a flocculated carbon nanotube film. Referring to FIG. 7, the flocculated carbon nanotube film may include a plurality of long, curved, and disordered carbon nanotubes entangled with each other. Furthermore, the flocculated carbon nanotube film can be isotropic. The carbon nanotubes can be substantially uniformly dispersed in the flocculated carbon nanotube film. Adjacent carbon nanotubes are acted upon by van der Waals attractive force to obtain an entangled structure with micropores defined therein. Because the carbon nanotubes in the flocculated carbon nanotube film are entangled with each other, the carbon nanotube layer employing the flocculated carbon nanotube film has excellent durability and can be fashioned into desired shapes with a low risk to the integrity of the carbon nanotube layer. A thickness of the flocculated carbon nanotube film may range from about 0.5 nanometers to about 1 millimeter.

Figure 8:
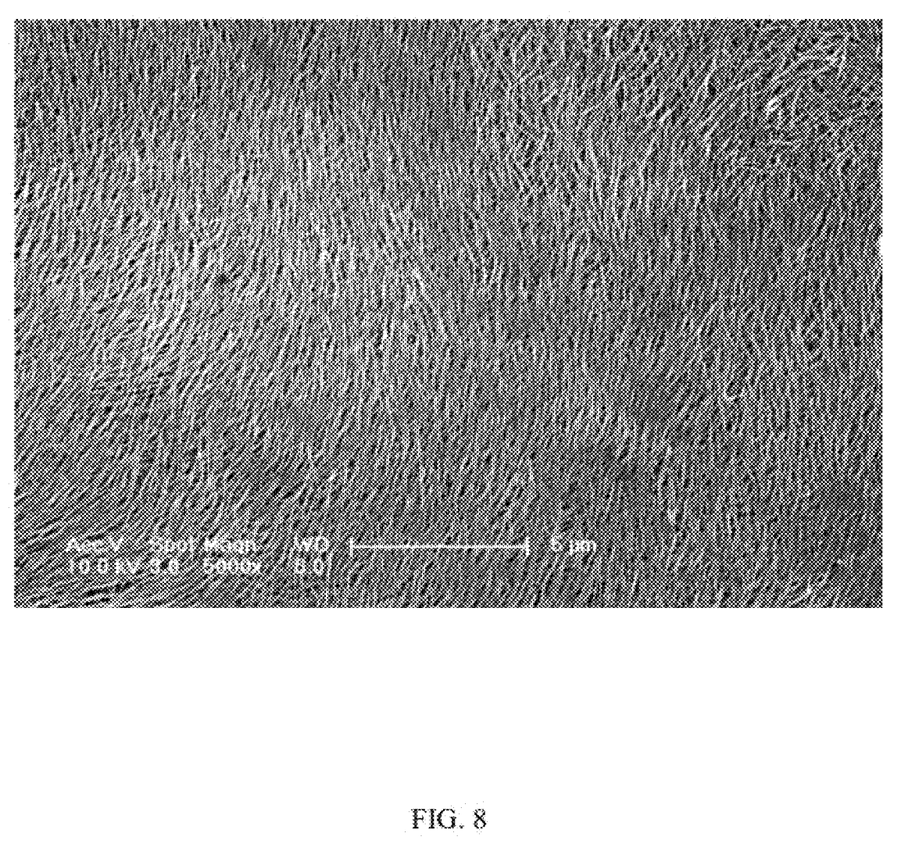
FIG. 8 shows an SEM image of a pressed carbon nanotube film.

Referring to FIG. 8, in other embodiments, the carbon nanotube film can be a pressed carbon nanotube film. The pressed carbon nanotube film is formed by pressing a carbon nanotube array. The carbon nanotubes in the pressed carbon nanotube film are arranged in a same direction different directions. The carbon nanotubes in the pressed carbon nanotube film can rest upon each other. Adjacent carbon nanotubes are attracted to each other and are joined by van der Waals attractive force. An angle between a primary alignment direction of the carbon nanotubes and a surface of the pressed carbon nanotube film is in a range from 0 degrees to 15 degrees. The greater the pressure applied, the smaller the angle obtained. In one embodiment, the carbon nanotubes in the pressed carbon nanotube film are arranged along different directions, the carbon nanotube layer can be isotropic. A thickness of the pressed carbon nanotube film may range from about 0.5 nanometers to about 1 millimeter.

In one embodiment, the carbon nanotube layer consists of four layers of drawn carbon nanotube films, and a cross angle of adjacent drawn carbon nanotube films is 90 degrees, and the diameter of the micropores in the carbon nanotube layer is 1.5 micrometers.

The tiny power 110 is configured to apply a voltage between the first carbon nanotube layer 112 and the second carbon nanotube layer 114, and a potential difference is formed between the first carbon nanotube layer 112 and the second carbon nanotube layer 114. Thereby, the electric field is existed between the first carbon nanotube layer 112 and the second carbon nanotube layer 114. In one embodiment, the tiny power 110 can be a button battery, and the voltage between the first carbon nanotube layer 112 and the second carbon nanotube layer 114 can be 1.5 V. In other embodiments, the voltage between the first carbon nanotube layer 112 and the second carbon nanotube layer 114 can be in a range from 1 V to 10 V. The first carbon nanotube layer 112 and the second carbon nanotube layer 114 are coupled with the tiny power 112 via lead wires (not shown).

Figure 9:
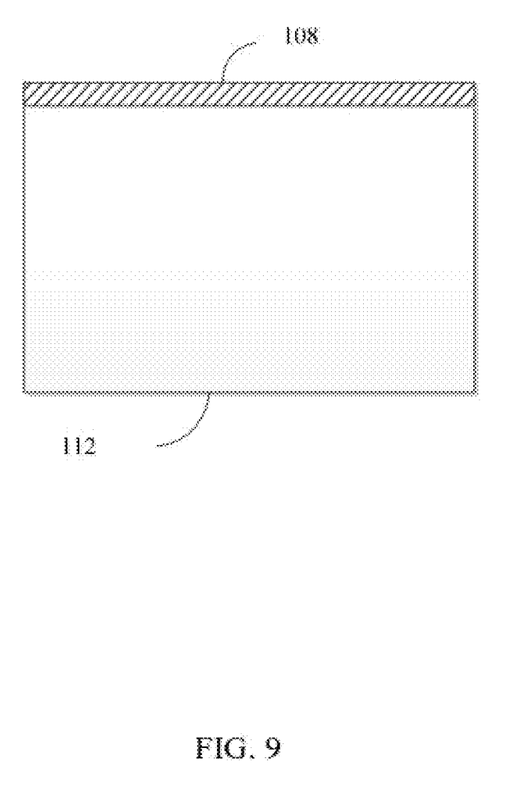
FIG. 9 is a schematic view of electrodes arrangement in an electrostatic adsorption mask according to another embodiment.
Figure 10:
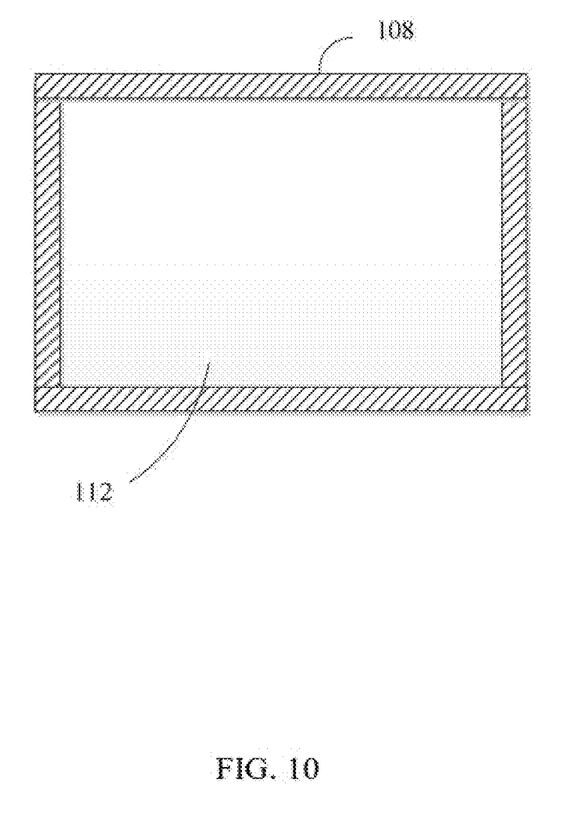
FIG. 10 is a schematic view of electrodes arrangement in an electrostatic adsorption mask according to yet another embodiment.

The filtering layer 106 further comprises a first electrode 108a and a second electrode (not shown). The first electrode 108a is electrically connected with the first carbon nanotube layer 112. Referring to FIG. 9, the first electrode 108a can have a liner structure and overlapped with a rim of the first carbon nanotube layer 112. Referring to FIG. 10, the first electrode 108a can have a ring structure and surrounds the periphery of the first carbon nanotube layer 112. It can be understood that, the first electrode 108a is an optional structure, and the first carbon nanotube layer 112 can be electrically connected to the tiny power 110 through wires.

The second electrode is electrically connected to the tiny power 110 through a wire, and the second electrode is disposed on the surface of the second carbon nanotube layer 114. Characteristics of the second electrode are the same as the first electrode 108, and will not be described again here.

A material of the first electrode 108a and the second electrode can be metal, alloy, indium tin oxide (ITO), antimony tin oxide (ATO), conductive silver paste, conductive polymer, conductive carbon nanotube, etc.

The electrostatic adsorption mask 100 can further include a support, which is arranged in the mask body so that the mask body can have a larger cavity used to expand the effective flow area, thereby reducing the wearer's breathing resistance. A material of the support can be plastic, metal, or the like.

When a wearer is wearing the electrostatic adsorption mask, the tiny power is turned on. At this time, an electric field exists between the first carbon nanotube layer and the second carbon nanotube layer inside the filtering layer. The electric field can absorb dust particles and charged bacteria or viruses. Therefore, the electrostatic adsorption mask can achieve a high-efficiency filtering effect by providing a filtering layer; at the same time, because the electrostatic adsorption mask does not block dust particles and charged bacteria or viruses via micropores in the electrostatic adsorption mask, therefore, the micropore diameter of the mask should not be too small, the breathing resistance of the mask will not be too large, and the wearer will feel more comfortable. For example, even if it is used as a PM2.5 mask, in the electrostatic adsorption mask provided by the present invention, the micropores of the filtering layer need not be smaller than 2.5 microns. Through electrostatic adsorption, PM2.5 particles can be directly adsorbed to achieve a filtering effect.

Depending on the embodiment, certain blocks/steps of the methods described may be removed, others may be added, and the sequence of blocks may be altered. It is also to be understood that the description and the claims drawn to a method may comprise some indication in reference to certain blocks/steps. However, the indication used is only to be viewed for identification purposes and not as a suggestion as to an order for the blocks/steps.

The embodiments shown and described above are only examples. Even though numerous characteristics and advantages of the present technology have been set forth in the foregoing description, together with details of the structure and function of the present disclosure, the disclosure is illustrative only, and changes may be made in the detail, especially in matters of shape, size, and arrangement of the parts within the principles of the present disclosure, up to and including the full extent established by the broad general meaning of the terms used in the claims. It will therefore be appreciated that the embodiments described above may be modified within the scope of the claims.

What is claimed is:

1. An electrostatic adsorption mask comprising:
two straps, a mask body, a filtering layer, and a tiny power; wherein the filtering layer is located in the mask body and comprises a first carbon nanotube layer, a second carbon nanotube layer and an insulated porous layer, the insulated porous layer is located between the first carbon nanotube layer and the second carbon nanotube layer, the first carbon nanotube layer and the second carbon nanotube layer are electrically coupled with the tiny power, and an electric field is existed between the first carbon nanotube layer and the second carbon nanotube layer.

2. The mask of claim 1, wherein the first carbon nanotube layer or the second carbon nanotube layer is a carbon nanotube layer comprising a plurality of carbon nanotubes joined with each other by van der Waals attractive force therebetween.

3. The mask of claim 2, wherein the carbon nanotube layer consists of one carbon nanotube film or at least two carbon nanotube films.

4. The mask of claim 3, wherein the carbon nanotube film comprises a plurality of successive and oriented carbon nanotubes joined end-to-end by van der Waals attractive force therebetween.

5. The mask of claim 4, wherein the first electrode and the second electrode are connected with the tiny power.

6. The mask of claim 2, wherein the carbon nanotube layer is a substantially pure structure of carbon nanotubes.

7. The mask of claim 2, wherein the carbon nanotube layer is a freestanding structure.

8. The mask of claim 1, wherein a voltage is applied to the first carbon nanotube layer and the second carbon nanotube layer via the tiny power.

9. The mask of claim 8, wherein a voltage difference between the first carbon nanotube layer and the second carbon nanotube layer is in a range from 1 V to 10 V.

10. The mask of claim 1, wherein the filtering layer comprises a plurality of micropores, and diameters of the plurality of micropores are in a range from 1 micrometer to 2.5 micrometers.

11. The mask of claim 1, wherein the tiny power is a button battery.

12. The mask of claim 1, wherein the filtering layer comprises a first electrode electrically connected with the first carbon nanotube layer and a second electrode electrically connected with the second carbon nanotube layer.

* * * * *